United States Patent [19]

Stadler et al.

[11] Patent Number: 4,683,222

[45] Date of Patent: Jul. 28, 1987

[54] N-GLYCOSYLATED CARBOXAMIDE DERIVATIVES AND THEIR USE FOR INFLUENCING THE BODY'S INHERENT DEFENCES

[75] Inventors: Peter Stadler, Elkhart, Ind.; Oswald Lockhoff, Leverkusen, Fed. Rep. of Germany; Hans-Georg Opitz, Wuppertal, Fed. Rep. of Germany; Klaus Schaller, Wuppertal, Fed. Rep. of Germany

[73] Assignee: Bayer Aktiengesellschaft, Leverkusen, Fed. Rep. of Germany

[21] Appl. No.: 725,060

[22] Filed: Apr. 19, 1985

Related U.S. Application Data

[63] Continuation of Ser. No. 481,210, Apr. 1, 1983, abandoned.

[30] Foreign Application Priority Data

Apr. 14, 1982 [DE] Fed. Rep. of Germany ....... 3213650

[51] Int. Cl.[4] ...................... A61K 31/70; C07H 15/12
[52] U.S. Cl. ......................................... 514/42; 536/22
[58] Field of Search ............................ 514/42; 536/22

[56] References Cited

U.S. PATENT DOCUMENTS 2,808,402  10/1957  Boettner .............................. 560/160

FOREIGN PATENT DOCUMENTS 0091645  10/1983  European Pat. Off. ............ 424/180

OTHER PUBLICATIONS

Chemical Abstracts, 78:136597t (1973).
Chemical Abstracts, 87:201958p (1977).
Chemical Abstracts, 90:72406t (1979).
Chemical Abstracts, 89:129847y (1978).

Primary Examiner—Johnnie R. Brown
Assistant Examiner—Elli Peselel
Attorney, Agent, or Firm—Sprung, Horn, Kramer & Woods

[57] ABSTRACT

The invention relates to N-glycosylated carboxamide derivatives of Formula I which are useful for influencing the body's inherent defenses, e.g. for increasing immune system antibodies. Also included in the invention are compositions containing said N-glycosylated carboxamide derivative of Formula I as active ingredients and methods for the use of said compounds and compositions.

18 Claims, No Drawings

N-GLYCOSYLATED CARBOXAMIDE DERIVATIVES AND THEIR USE FOR INFLUENCING THE BODY'S INHERENT DEFENCES

This is a continuation of application Ser. No. 481,210, filed Apr. 1, 1983, now abandoned.

The present invention relates to compounds of the general formula I

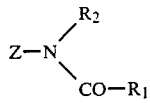

In this formula, $R_1$ denotes hydrogen or an optionally substituted straight-chain or branched, saturated or singly or multiply unsaturated alkyl radical having one to 30 carbon atoms, it being possible for this radical $R_1$ also to be interrupted by up to 5, preferably 1 or 2, O, S and/or N, with the proviso that —$COR_1$ does not represent an acyl group having 1–5 C atoms when $R_2$ denotes alkyl having 10–20 C atoms.

When the chain is interrupted by N, this nitrogen carries either H or a $C_1$–$C_{20}$, preferably $C_1$–$C_5$, alkyl radical or a —CO—alkyl radical, this alkyl group having 1–20, preferably 1–5, C atoms.

Preferably, $R_1$ represents an alkyl or alkenyl radical having 1 to 21 carbon atoms, preferably having 9 to 21 C atoms. Examples of saturated radicals which may be mentioned here are methyl, ethyl, propyl, i-propyl, butyl, i-butyl, n-penyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, docosyl, ethylpentyl, methyldecyl, i-propyldecyl and methyltridecosyl.

Examples of unsaturated radicals are ethylene, propen-1-yl, propen-2-yl, i-butenyl, buten-1-yl, buten-2-yl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 5-octenyl, 7-octenyl, 1-nonenyl, 3-nonenyl, 5-nonenyl, 7-nonenyl, 1-decenyl, 5-decenyl, 9-decenyl, 8-heptadecenyl, 1,3-butadienyl, 1,3-pentadienyl, 1,4-pentadienyl, 2,4-pentadienyl, 1,3-heptadienyl, 2,4-heptadienyl, 1,3-octadienyl, 1,3-nonadienyl, 2,4-decadienyl 8,11-heptadecanedienyl, and 8, 11,14-heptadecanetrienyl. In general, the longer chain unsaturated radicals are preferred, especially the singly or doubly unsaturated alkenyls having 7–21 C atoms.

The unsaturated hydrocarbon radicals can in this context be present as pure cis or trans isomers or as mixtures of isomers.

Examples for cases in which the hydrocarbon radicals $R_1$ in formula I are interrupted by O, S and N or corresponding groups of atoms or are substituted by groups containing these atoms or by halogen atoms, are the methoxyethyl, 2-(2-methoxyethoxy)-ethyl, 2-[2-(2-methoxyethoxy)ethoxy]-ethyl, hydroxyheptadecenyl, oxobutyl, aminodecyl, N-methylaminodecyl, fluoromethyl, β-hydroxytridecyl or mercaptoethyl radical.

The hydrocarbon radicals $R_1$ in formula I can also contain phenyl radicals, it being possible for these phenyl radicals optionally also to be substituted by one two or three substituents from the series nitro, lower alkyl having 1 to 7, especially 1 to 4 and particularly 1 or 2 carbon atoms or by 1–5 halogen atoms (preferably bromo, chloro and particularly fluoro atoms).

$R_2$ in formula I represents hydrogen or a straight-chain or branched, saturated or singly or multiple unsaturated alkyl, cycloalkyl (preferably cyclopentyl or cyclohexyl) alkylcycloalkyl, preferably cyclohexyl, or cyclopentyl which is methylated or ethylated or an aralkyl radical having up to 30 carbon atoms and in which the aryl portion is preferably mono- or bi-cyclic carbocyclic aryl (such as phenyl, biphenyl or naphthyl) and the alkyl portion contains 1 to 4, preferably 1 to 2, carbon atoms, it being possible in the radical $R_2$ for individual methylene or methine groups to be replaced by up to 5 oxygen or sulphur atoms or N, NH or N-lower alkyl groupings. Individual hydrogen atoms in the alkyl, cycloalkyl or aralkyl radicals can also be substituted by up to 5 oxygen-containing groups or halogen (preferably chloro, fluoro or bromo) atoms.

Examples in which $R_2$ in formula I represents a straight-chain or branched, optionally singly or multiply unsaturated alkyl radicals are those mentioned for $R_1$.

Methyl, propyl, hexyl, decyl, undecyl, dodecyl, tridecyl, tetradecyl, pentadecyl, hexadecyl, heptadecyl, octadecyl, nonadecyl, docosyl, myricyl, ethylhexyl, isobutyl, propenyl, octenyl, hexadienyl, docosenyl, dimethylhexenyl and 2-(cyclohexyl)-ethyl may be particularly mentioned. The unsaturated hydrocarbons can be present as pure cis or trans isomers or as a mixture of isomers. Examples of hydrocarbon radicals $R_2$ substituted by groups containing oxygen aroms are hydroxypropyl and hydroxydimethyloctyl, and examples of hydrocarbon radicals interrupted by oxygen atoms are alkoxyalkyl radicals or (alkoxyalkoxy)alkyl radicals, such as metoxybutyl or butoxypropyl or ethoxyethoxyethyl, an example of a radical interrupted by N and O is 2-(N-morpholino)-ethyl, and trifluoromethylethyl may be mentioned as an example of a halogen-substituted hydrocarbon radical.

Aralkyl for $R_2$ in formula I is, for example, aryl-lower-alkyl, such as benzyl, phenethyl or phenylhexyl, it being possible for the phenyl nucleus optionally to be substituted once or several times, preferably once or twice, for example by lower alkyl, trifluoromethyl, halogen, hydroxyl or lower alkoxy.

Lower alkyl or alkoxy as used herein and unless otherwise specified are understood to define those radicals which contain 1–5, preferably 1–3 carbon atoms.

Z in formula I denotes a glycosyl radical which, in the compounds according to the invention, is always bonded to the amide nitrogen via the anomeric carbon atom, the glycosyl radicals according to the invention being particularly understood to include mono-, di- and oligosaccharide radicals, particularly mono- and di-saccharides, in which it is optionally possible for one or more hydroxyl groups to be replaced by amino groups, acylamido groups, azido groups, hydrogen, nitro, thiol groups or lower alkoxy or halogen, and it being possible for the glycosyl radicals also to be present in the form of the corresponding uloses, ulose derivatives, uronic acids or of uronic acid derivatives.

The glycosyl radicals Z in formula I are preferably present, according to the invention, in the pyranosyl or the furanosyl form, the relevant monosaccharide, disaccharide or oligosaccharide radicals preferably being constructed of tetroses, pentoses, hexoses and heptoses.

Examples of monosaccharide radicals according to the invention are glucopyranosyl, galactopyranosyl, mannopyranosyl, glucofuranosyl, ribofuranosyl, arabinopyranosyl or lyxopyranosyl, or D-glycero-D-glucoheptopyranosyl radicals. Examples of di- and oligosaccharide radicals which can be mentioned are maltosyl, maltotriosyl, maltotetraosyl, lactosyl, cellobiosyl, melibiosyl, or 6-O-($\alpha$- or $\beta$-ribofuranosyl)-glucopyranosyl radicals, that is to say thus carbohydrate systems which are constructed of sugars having different C numbers and in which it is possible for the sugars to be present in the pyranose and/or furanose form. The glycosidic bonds between the individual sugar structural elements can be present in the $\alpha$- and-/or $\beta$-form and the glycosidic link of the individual sugar structural elements can take place from an anomeric carbon atom both via the primary OH group and also via one of the secondary hydroxyl groups of the saccharide part functioning as an aglycone.

Examples of mono-, di- and oligosaccharide radicals, in which one or more OH groups are replaced by amino groups, acylamido groups, azido groups, hydrogen, nitro, thiol groups, lower alkoxy or halogen, which may be mentioned are 2-acetylamido-2-deoxyglucopyranosyl, 2-amino-2-deoxyglucopyranosyl, 4-azido-4-deoxyglucopyranosyl, 4-stearoylamido-4-deoxy-D-glucopyranosyl, 4-dodecylamido-4-deoxy-D-glucopyranosyl, 6-hexadecanoylamido-6-deoxy-D-galactopyranosyl, 2,6-diamino-2,6-dideoxyglucopyranosyl, 6,6'-diamino-6,6'-dideoxymaltosyl, 6-amino-6,6'dideoxylactosyl, 6-deoxymannopyranosyl, 2-deoxyribofuranosyl, fucosyl, 5-fluoro-5-deoxyribofuranosyl, 6-O-methylglucopyranosyl, 6-deoxy-6-thioglucopyranosyl and 3-deoxy-3-nitrogalactopyranosyl.

If the glycosyl radicals are present in the form of uronic acids or uronic acid derivatives, they are glycuronic acids having a free carboxyl group or having a carboxyl group esterified by alkyl or are glycuronamide derivatives having an unsubstituted or substituted nitrogen atom. Examples of appropriate sugars are galacturonic acid, methyl glucuronate, glucuronamide or N-dodecylglucuronamide.

The compounds of the formula I contain several chiral carbon atoms and are present as optically pure diastereomers or as mixtures of diastereomers. The compounds of the formula I according to the invention are thus carboxamides or N-alkylated or N-aralkylated carboxamides, which each carry a simple or modified mono-, di- or oligosaccharide radical N-glycosidically on the amide nitrogen, that is to say bonded via the anomeric carbon atom.

Very particularly preferred compounds are those shown by exemplary embodiments, in particular those shown in Examples 12, 13, 14, 15, 16, 17, 18, 19, 23, 25, 33, 34, 35, 37, 39, 40, 42, 43, 45, 46, 48, 49, 50, 53, 54, 55, 56, 57 and 58.

The invention also relates to processes for the preparation of the compounds of the formula I. In this, the sugars comprised by Z in formula 1 are reacted, either in the free, that is to say unprotected, form or in the form of protected and optionally activated derivatives, initially with an amino compound $R_2$—$NH_2$, either in the free form or in the form of a suitable acid addition salt, having the meaning described above for $R_2$, and the glycosylamine thus obtained is subsequently acylated with an activated, as is customary for acylation reactions, carboxylic acid derivative, which is protected, if appropriate, on functional groups, the protective groups which are, if appropriate present in the reaction product thus obtained are split off and, in this manner, the compounds of the formula I according to the invention are obtained, which if necessary, can be purified by chromatography, recrystallisation, extraction or the like.

In a preferred embodiment of the process according to the invention, in a first process step, the unblocked sugar Z—OH, OH representing the anomeric hydroxyl group, having the meaning of Z described in formula I, is reacted in a manner known per se in a suitable solvent, or even without solvent, optionally in the presence of a catalyst, at temperatures between 0° C. and 80° C., with 1 to 10 equivalents of the relevant amine $R_2$—$NH_2$, and the relevant glycosylamines Z—NH—$R_2$ are usually obtained in high yield as amorphous or crystalline solids or as viscous syrups after working up.

In the second process step, the glycosylamine Z—NH—$R_2$ is then reacted with 1–10 equivalents of a carboxylic acid derivative of the formula $R_1$—CO—X, in which $R_1$ has the abovementioned meaning and X designates halogen or a leaving group customary in acylation reactions, preferably an activating ester radical, or a group O—CO—(O)$_n$—$R_1$(n=0 or 1), having the above meaning for $R_1$, the reaction being carried out in an organic or aqueous-organic solvent at temperatures between 0° C. and 50° C., optionally in the presence of a base, and, after completion of the reaction, the reaction product is worked up in a customary manner.

In the case where one or more free amino groups are present in the carbohydrate radical Z, these are provided with an amino protective group in a manner known per se before reaction with the amine $R_2$—$NH_2$.

Suitable amino protective groups are those groups customarily used in sugar and peptide chemistry (see, for example, HOUBEN-WEYL Methoden der organischen Chemie [Methods in organic chemistry], volume XV, Georg Thieme Verlag, Stuttgart, 1974), which, on the one hand, are stable under the given reaction conditions but, on the other hand, after the preparation of the relevant N-glycoside and its subsequent acylation with a carboxylic acid derivative $R_1$—CO—X, with the abovementioned meaning for $R_1$, can be split off again so selectively that the desired end product of the formula I is obtained, that is to say without the acylamino group containing in the end product of the formula I being after cleaved. Preferred examples are acyl group of the type

B denoting trichloromethyl or trifluoromethyl or of the type

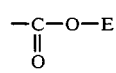

E, for example, representing trichloroethyl or tertiary butyl, or sulphenyl groups of the type

—S—G

G representing phenyl, substituted phenyl or di- or triphenylmethyl and "substituted phenyl" designating a phenyl radical which is substituted by one, two or three substituents from the series nitro, lower alkyl or by 1 or 5 halogen atoms, preferably chlorine or fluorine atoms. Examples which may be mentioned are the 2,4,5-trichlorophenylsulphenyl and the onitrophenylsulphenyl radical.

The introduction of these protective groups into amino compounds and their later splitting off to liberate the desired amino groups are known and are described, for example, in the literature reference cited above.

In another embodiment of the process for the preparation of those products of the formula I in which one or more free amino groups are present in the glycosyl radical Z, sugar derivatives Z—OH are employed as starting products in which the amino group or the amino groups are initially present in the form of azido radicals, that is to say in a masked form. In the final step of the preparation of the compounds of the formula I, these azido groups are converted reductively in a manner known per se into amino groups it being necessary to take care that those reducing agents are used which do not attack other groups sensitive to reduction which may be present in the molecule.

Appropriate azido sugars and their preparation are known (see, for example, Methods in Carbohydrate Chemistry, vol. I, 242–246, Academic Press, 1962 New York and London). Hydride donors, such as, for example, sodium boranate or lithium alanate, catalytically excited hydrogen or triphenylphosphine in methanol-/ammonia/pyridine or hydrogen sulphide or mercaptans in protic solvents can be used for the reduction.

All common organic solvents, preferably lower alkanols, such as ethanol or isopropanol but also water or aqueous lower alkanols can be used as the solvent.

The reactions are optionally carried out with the addition of organic acids, such as, for example, acetic acid or inorganic acids, such as, for example, sulphuric acid, or with the addition of organic bases, such as, for example, pyridine or inorganic bases, such as, for example, ammonia. The reaction is carried out at temperatures between 0° and 120° C., preferably 10° C. to 40° C., optionally under elevated pressure and/or inert gas.

In the case where one or more OH groups in the carbohydrate part Z in the final products of the formula I according to the invention are replaced by one or more acylamido groups, the sugars Z—OH are employed from the start in the form of the corresponding acylamido sugars. The acylamido sugars are then initially reacted at the anomeric centre with the above-mentioned amines to give the corresponding acylamido-glycosylamines and, in the second reaction step, are acylated on the C-1 amino group of the sugar moiety to give N-(acylamidoglycosyl)-amides of the formula I.

Another procedure for the preparation of compounds of the formula I, in which Z represents a sugar radical substituted with one or more acylamido groups, consists of reacting aminodeoxy sugars, which carry the amino group on a carbon atom other than the anomeric carbon atom, with amines of the formula R$_2$—NH$_2$ to give (aminodeoxyglycosyl)amines, which then, in the second reaction step, are acylated twice or, where appropriate, several times to give N-(acylamidoglycosyl)amides of the formula

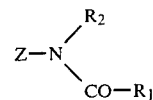

Furthermore it is also possible to obtain the compounds of the formula I, in which Z represents a sugar radical substituted with one or more acylamido groups, by splitting off the temporary amino protective groups, by the customary methods, in derivatives of the formula I, in which Z initially represents an amino sugar blocked by one or more temporary amino protective groups of the type mentioned above

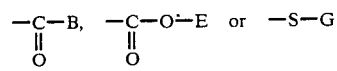

to give the corresponding N-(aminodeoxyglycosyl)amides, and the latter are then reacted with activated carboxylic acid derivatives to give the corresponding N-(acylamidoglycosyl)amides of the formula I

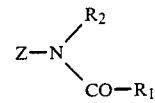

Another procedure for the preparation of N-(acylamidoglycosyl)amides of the formula I consists of reacting N-(azidoglycosyl)amides of the formula I by the customary methods to give the N-(aminoglycosyl)amides of the formula I and then acylating the latter with activated carboxylic acid derivatives to give N-(acylamidoglycosyl)amides of the formula I.

The first process step in the preparation of the compounds of the formula I according to the invention is thus the reaction of a sugar, Z—OH, at the anomeric carbon atom, with an amine of the type R$_2$—NH$_2$, with water being split off, to give the relevant glycosylamine.

Amines R$_2$—NH$_2$, which are liquid at room temperature, can be reacted directly, that is to say without solvent, with the sugar. This reaction is carried out at temperatures between 0° C. and 100° C., preferably at 25° C. to 70° C. Suitable catalysts are mineral acids, such as, for example, hydrochloric acid, sulphuric acid or nitric acid, or short-chain carboxylic acids, such as acetic acid or propionic acid, which are employed in amounts of 0.001 to 0.05 equivalents.

It is possible in every case, and it is also preferred for amines R$_2$—NH$_2$, which are solid at room temperature, to carry out the preparation of the glycosylamines in the presence of a solvent. The reaction is then preferably carried out in the presence of a diluent which is inert under the reaction conditions and which preferably is of such a nature that at least either the reactants or the reaction product dissolve in it.

Suitable solvents are alcohols, particularly C$_1$-C$_3$-alkanols, such as methanol, ethanol, 1-propanol and 2-propanol; ethers, such as di-C$_1$-C$_2$-alkyl ethers, tetrahydrofuran and dioxane, and also dimethylformamide, the addition of water being preferred except that when using the alcohols. In addition, preferably for short-chain amines R$_2$—NH$_2$ water alone is also suitable as the solvent. It can also be advantageous to use the alkanols mixed with water.

When using solvents in the preparation of the glycosylamines, the reaction temperatures are between −10° C. and 120° C., preferably between 30° C. and 70° C.

The relevant diluent can be added, as chosen, before or during the reaction. Addition before the reaction is to be preferred for long-chain amines $R_2$—$NH_2$.

The glycosylamines, which have been prepared as described above, crystallize out either immediately or after cooling down and can be precipitated or brought to crystallize by the addition of suitable, preferably less polar auxiliary solvents, such as acetone, diethyl ether, cyclohexane, ethyl acetate or petroleum ether, if necessary with cooling, and any excess amine $R_2$—$NH_2$ present can be removed by washing or recrystallization of the product in a manner known per se.

The second process step in the preparation of the compounds of the formula I according to the invention is the selective N-acylation of a glycosylamine, obtained as described above, with a carboxylic acid derivative of the formula $R_1$—CO—X, with the meaning of $R_1$ and X given above. Carboxylic acid derivatives $R_1$—CO—X which are to be preferred as known per se are anhydrides, activated esters and acid halides, preferably chlorides.

These acylating agents are preferably reacted with the glycosylamines in the presence of a diluent in which the reactants are dissolved completely or even only partially.

Organic or inorganic solvents are suitable, preferably those which, under the reaction conditions, suppress or prevent as far as possible side reactions. The reaction can be carried out both in organic solvents, such as ethers, for example tetrahydrofuran and dioxane, or alcohols, for example, ethanol and propanol, or ketones, for example, acetone or methyl ethyl ketone, or in dimethylformamide, ethyl acetate or pyridine and also in mixtures of these solvents with one another and/or with water. In general, the use of anhydrous solvents is to be preferred.

The acylating agents $R_1$—CO—X are employed in 1–10 equivalents relative to glycosylamine, the use of 1–3 equivalents being preferred.

The acylation reactions can, preferably when using acid halides and anhydrides, be carried out in the presence of basic auxiliaries. All basic compounds customary in organic synthesis can be used, such as, for example, tertiary aliphatic or aromatic amines or alkali metal and alkaline earth metal hydroxides or carbonates, such as sodium hydroxide solution, sodium carbonate or calcium carbonate.

The acylations are carried out at temperatures between about −30° C. and +80° C., preferably between −10° C. and +20° C.

The amides obtained in this manner are isolated by processes known per se in the form of crystalline or amorphous solids or as viscous syrups and, if necessary, are purified by recrystallisation, chromatography, extraction and the like.

In the case of compounds with protected amino groups in the glycosyl moiety, the protective groups are split off in a manner known per se.

The following formula diagram is intended to illustrate by example one of the preferred embodiments of the preparation according to the invention of compounds of the formula I.

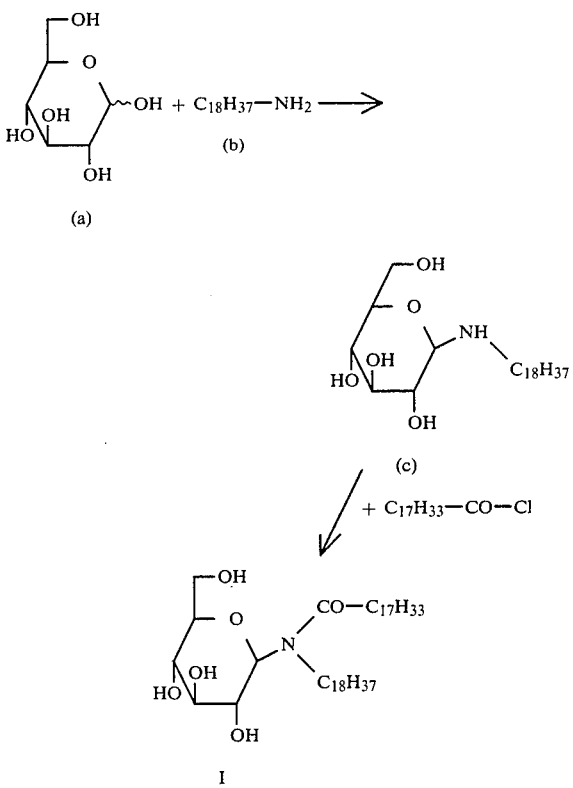

In the first process step, glucose (a) is reacted with octadecylamine (b) to give N-octadecyl-β-D-glucopyranosylamine (c) which, in the second process step is acylated with oleyl chloride to give N-octadecyl-N-oleyl-β-D-glucopyranosylamine (I).

The compounds of the formula I according to the invention in which $R_2$ denotes hydrogen can be prepared by initially reacting a sugar Z—OH or an N-protected amino sugar, with the meaning of Z given above, with ammonia, by which means glycosylamines of the formula Z—$NH_2$ or their protected form are obtained. The reaction can be carried out in a manner known per se both in liquid ammonia and also in solutions of ammonia in suitable solvents (reference, for example, HODGE and MOY, J. Org. Chem. 28, 2784 (1963)), high concentrations of ammonia and temperatures of −70° C. to +10° C. being preferred. Suitable solvents are organic solvents or organic/aqueous systems, alkanols, particularly methanol and ethanol, being preferred.

In this manner, ribose, for example, in methanol with ammonia at 0° C. provides crystalline β-D-ribopyranosylamine according to the following equation:

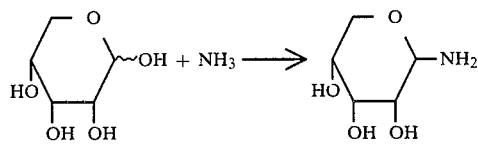

The subsequent N-acylation of the glycosylamines Z—$NH_2$ or the N-protected glycosylamines is carried out with a carboxylic acid derivative of the formula $R_1$—CO—X with the meaning of $R_1$ given above.

These carboxylic acid derivatives are, for example, anhydrides, acid halides or activated esters, preferably acid chlorides. They are preferably employed with the glycosylamines Z—$NH_2$, protected if necessary, in the presence of a diluent in which the reactants are completely or even only partially dissolved.

Suitable solvents are those mentioned above.

The compounds of the formula I according to the invention with the meaning of hydrogen for $R_2$ are obtained in the manner described above in high yields.

The compounds of the formula I, in which $R_2$ denotes hydrogen, can also be prepared by acylation of those glycosylamines in which Z designates a chemically changed sugar radical, in which all hydroxyl groups present in the molecule are protected with a protective group which can be easily split off.

Protective groups which can be easily split off are known from peptide chemistry and sugar chemistry.

A preparative example is given in the following formula diagram.

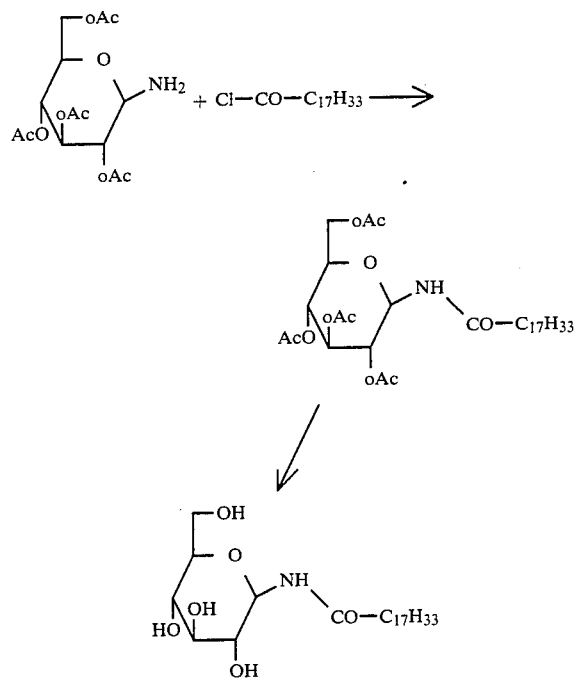

Tetra-O-acetyl-β-D-glucopyranosylamine is acylated with oleyl chloride in tetrahydrofuran in the presence of sodium carbonate. The N-acyl derivative is O-deacetylated with triethylamine in aqueous methanol.

The invention also relates to salts of the compounds of the formula I where such salts can be formed. These are primarily the customarily pharmaceutically usable, non-toxic salts, for example alkali metal or ammonium salts.

The compounds of the present invention have valuable pharmacological properties, in particular a pronounced resistance-increasing effect. It has been found that the compounds of the present invention increase the antibody synthesis of the immune system and also strengthen the non-specific defences inherent to the host. This can be shown by means of the design of experiment described below.

Potentiation of the humoral immunity against sheep erythrocytes (SE).

It is experimentally possible to permit the entire course of antibody synthesis to take place in vitro. For this purpose, cultures of spleen cells of the mouse are immunised with sheep erythrocytes (SE). 5 days later, the anti-SE antibody-forming cells are determined. Compounds of the present invention, as shown in Table 1, are capable, surprisingly, of increasing the number of antibody-forming cells as a function of the dose in the range 1–30 μg/ml.

TABLE 1

Effect of selected N—glycosylated carboxamide derivatives on the synthesis of antibodies against sheep erythrocytes in vitro.

| Compound according to Example | Antibody-secreting cells/culture as a function of the dose (μg/ml) | | | | |
|---|---|---|---|---|---|
| | 0 | 1 | 3 | 10 | 30 |
| 15 | 2620 | 2840 | 4040 | 6760 | 12330 |
| 18 | 2030 | 2350 | 3660 | 7580 | 10300 |
| 19 | 1390 | 2090 | 2550 | 8760 | 12680 |
| 35 | 2700 | 3680 | 4850 | 5200 | 8160 |
| 23 | 2760 | 4000 | 5740 | 6920 | 10600 |

Potentiation of the humoral immunity in vivo: increase in the production of antibodies against sheep erythrocytes in the mouse.

NMRI mice were immunised by intraperitoneal (i.p.) injection of $10^7$ of SE. 5 days later, the spleens were removed and the number of anti-SE antibody-secreting lymphocytes was determined. In a second design of experiment, the titer of the haemagglutinating antibodies in the serum of the animals was determined. At the dose used, the SE are suboptimal for the receiving animals, that is to say they are only capable of stimulating a small number of lymphocytes to synthesise antibodies. Additional treatment of the animals with compounds of the present invention is able to increase, on single intraperitoneal or subcutaneous (s.c.) administration of 1.0–100 mg/kg, the number of antibody-forming cells by a factor of 5 to 10 above the control value and significantly to increase the antibody titer in the serum of the animals.

The immunostimulant effect of the compounds mentioned is, in contrast to other bacterial immunostimulants (for example LPS from Gram-negative microorganisms), dependent on the antigen, that is to say the injection of the new compounds only results in an increase in the anti-SE titer in SE-immunised mice, but not in non-immunised mice.

Potentiation of the humoral immunity in vivo: increase in the production of antibodies against ovalbumin.

NMRI mice are immunised by intraperitoneal injection of 50 μg of ovalbumin on day 0. 7, 14 and 21 days later, serum samples are removed and investigated for their content of anti-ovalbumin antibodies by means of passive haemagglutination. At the dose used, ovalbumin is sub-immunogenic for the mice, that is to say it is capable of inducing only a very small production of antibodies, if at all. Treatment of the mice with particular immunopotentiating substances before or after administration of the antigen leads to an increase in the titer of antibody in the serum. The effect of treatment is expressed by the score achieved, that is to say by the total of the $\log_2$ titer differences on the three days of blood sampling.

In this test, the compounds of the formula I are able significantly to increase the production of antibodies against ovalbumin on intraperitoneal or subcutaneous administration of 1-100 mg/kg on the day of immunisation with ovalbumin.

Activation of macrophages

Macrophages are of central importance in the non-specific defence processes. They react to an antigen characteristically with an increased metabolism (macrophage activation), which can be primarily detected by increased secretory outputs. It has been possible to show that the compounds mentioned bring about, preferably with an antigen, such as, for example, *Candia albicans*, an increase in the macrophage activation. The release of superoxide, which has a cytotoxic effect, was measured. It emerged that the compounds of the type mentioned are able to increase the production of superoxide by at least a factor of 2.

Tolerance

Although compounds of the type described display their potentiating effect on the mouse, for example, after a single dose of only 10 mg/kg i.p., or perorally, no toxic effects are observed even on administration of 100 mg/kg. The substances mentioned thus have a good tolerance.

The compounds according to the invention have the ability of, on the one hand, when mixed with an antigen, increasing its immunogenicity and, on the other hand, on systemic administration, increasing the immunological reactivity of the treated organism. Moreover, the substances mentioned are able to activate the lymphocytes responsible for antibody formation.

The new compounds can thus be used as adjuvants mixed with vaccines to improve the success of vaccination and to increase the immunity-mediated protection against infection by bacterial, viral or parasitic pathogens.

Furthermore, the compounds described, mixed with the most diverse antigens, are suitable as adjuvants in the experimental and industrial production of antisera for therapy and diagnosis.

Moreover, the new compounds can be used, even without simultaneous administration of antigen, to promote defence reactions, which are already taking place subliminally, in warm-blooded animals. Thus the compounds are particularly suitable for stimulation of the body's inherent defences, for example for chronic and acute infections or for selective (antigen-specific) immunodeficiency, as well as for congenital and also for acquired general (that is to say not antigen-specific) immunodeficient states, as occur in old age, in the course of severe primary disorders and, in particular, after therapy with ionising radiation or with substances having immunosuppressive activity. The substances mentioned can thus preferably also be administered in combination with anti-infective antibiotics, chemotherapeutics or other medical treatments in order to counteract immunological damage. Finally, the substances described are also suitable for the general prophylaxis against infectious diseases in warm-blooded animals.

The compounds according to the invention increase the survival rate in the animal model of systemic mouse candidosis

Description of experiments

Mice of type SFF-CF$_1$ were inoculated intravenously with $2-6 \times 10^5$ logarithmically growing cells of *Candida albicans*, suspended in physiological saline. The first symptoms of disease are recognisable in untreated control animals starting with the 3rd day after inoculation. The first animals die of acute renal failure up to the 5th day and, as a rule, more than 80% of the untreated animals have died up to the 14th day after inoculation. In this test, the compounds of the formula I act both to delay disease and also therapeutically. A significant action delaying disease was achieved when the substances was each administered once 24 hours before inoculation in concentrations of 1-50 mg/kg of body weight, preferably intraperitoneally but also orally.

TABLE 2

Survival rates of Candida-inoculated CF$_1$ mice after i.p. pretreatment with the compounds stated

| Compound Preparation Example | Survival rate of the control animals on the 14th day | Survival rate of the pretreated animals on the 14th day |
|---|---|---|
| 14 | 1/10 | 4/10 |
| 43 | 1/10 | 4/10 |
| 45 | 0/10 | 4/10 |
| 48 | 0/10 | 6/10 |
| 49 | 0/10 | 4/10 |
| 56 | 0/10 | 4/10 |
| 57 | 0/10 | 4/10 |
| 58 | 0/10 | 6/10 |

A statistically significant prolongation of the survival time was observed in the treated animals compared to the untreated controls. About 50% of the treated animals survived a period of observation of 14 days, compared with about 10% of untreated control animals.

A therapeutic effect was achieved when the animals were treated orally or intraperitoneally once a day, starting with the day of inoculation, for 3 days with, in each case, 1-30 mg/kg of body weight of the preparation.

In the treated animal groups, about 60% of the animals survived up to the 14th day after inoculation, compared to 20% of the untreated control animals.

The prophylactic and therapeutic effectiveness of the compounds of the formula I in the animal model of mouse candidosis allows it to be assumed that the substance has a broad defence-stimulating effect, which leads to better control, not only of infections by yeasts, but also generally microbial pathogens in warm-blooded animals. Thus, it appears to be justified to designate the substance as having anti-infective activity, especially since there are no indications that the substance has antifungal activity.

The compounds according to the invention can be used alone as a propylactic for the defence against existing injections or in combination with an antibiotic therapy to increase the therapeutic effect of antibiotics and chemotherapeutics (for example penecillins, cephalosporins, aminoglycosides etc.) in infected warm-blooded animals.

It has been found that inoculations of the mouse with pathogenic organisms, which lead to the death of the experimental animals within 24-48 hours, could be treated and a prophylactic treatment, preferably intraperitoneal, with 1-80 mg/kg of the compounds of the formula I according to the invention. This applies to a large number of Gram-positive (for example Staphylococci) and Gram-negative (for example *E. coli*, Klebsiella, Proteus and Pseudomonas) pathogens. This list is to be taken as an example and by no means restrictive. Thus, for example, mice which have been inoculated with the pathogenic strain Klebsiella 63, after treatment (for example 18 hours before inoculation) with 20 mg/kg of the compound of Example 17 according to the invention survive this infection to the extent of 80–90%, whilst only 0–30% of the untreated control animals survived.

The compounds according to Examples 14, 19, 33, 37, 43, 49, 50, 53 and 58 also gave similar results.

It was possible to show in a further experiment that the therapeutic effectiveness of antibiotics can be increased by the compounds according to the invention (Table 3). Thus, mice were inoculated with the strain *Pseudomonas W*. This inoculation led to the death of most of the control animals within 24 hours. A further group was treated with 4 mg/kg of sisomicin 30 hours after inoculation. It was possible to show that it was possible significantly to improve the therapeutic effectiveness of the sisomicin in the experimental group which had been treated with 20 mg/kg of the compound of Example 17 according to the invention.

TABLE 3

Number of surviving animals (percent) on treatment with Example 17 in combination with sisomicin for the therapy of an inoculation with Pseudomonas W. of $CF_1$ mice.

| Preparation | % of surviving animals on | | |
|---|---|---|---|
| | 1st, | 3rd and | 5th day |
| | | after inoculation | |
| (1) Compound according to Example 17 20 mg/kg | 90 | 50 | 40 |
| (2) Sisomicin 4 mg/kg | 50 | 30 | 30 |
| (1) Compound Example 17/ 20 mg/kg + Sisomicin/4 mg/kg | 100 | 80 | 80 |
| Inoculation control | 25 | 15 | 15 |

(1) intraperitonal 18 hours before inoculation
(2) 30′ after inoculation s.c.

Similar results were also found for compounds according to Examples 14, 19, 33, 37, 43, 49, 50, 53 and 58.

The pharmaceutical preparations of the present invention are preferably tablets or gelatine capsules which contain the active compounds together with diluents, for example lactose, dextrose, sucrose, mannitol, sorbitol, cellulose and/or lubricants, for example, diatomaceous earth, talc, stearic acid or salts thereof, such as magnesium or calcium stearate, and/or polyethylene glycol. Tablets likewise contain binders, for example magnesium aluminium silicate, starches, such as maize, wheat, rice or arrowroot starch, gelatine, tragacanth, methylcellulose sodium carboxymethylcellulose and/or polyvinylpyrrolidone, and, if desired, disintegrants, for example starches, agar, alginic acid or a salt thereof, such as sodium alginate and/or effervescent mixtures, or adsorption agents, dyestuffs, flavourings and sweeteners. Injectable preparations are preferably isotonic aqueous solutions or suspensions. Suppositories, ointments or creams are primarily fatty emulsions or suspensions. The pharmaceutical preparations can be sterilised and/or contain auxiliaries, for example preservatives, stabilisers, wetting agents and/or emulsifiers, solubilisers, salts for regulating the osmotic pressure and/or buffers. The present pharmaceutical preparations, which, if desired, can contain other pharmacologically valuable substances, are produced in a manner known per se, for example by conventional mixing, granulating or coating processes, and contain from about 0.1% to about 75%, in particular from about 1% to 50% of the active substances mentioned.

The orally administered preparations of the present invention can also be provided with a coating resistant to gastric juices.

The compounds according to the invention, being resistance-increasing and immunopotentiating agents, can be used for the treatment of chronic and acute infections (for example bacterial, viral and parasitic) and malignant tumors. They can also by used as adjuvants for vaccination, for stimulation of phagocytosis and for disregulation of the defence and immune system.

The following examples illustrate the invention described above, but they are not intended to restrict its extent in any manner.

The invention also relates in general to the salts of the compounds I having any other salt-forming groups, for example free carboxyl groups, primarily pharmaceutically usable non-toxic salts, for example metal or ammonium salts.

EXAMPLES

Thin-layer chromatography (TLC) was carried out on silica gel TLC ready-coated plates (E. Merck, Darmstadt) and the preparative separations were carried out with silica gel 60 (Merck, Darmstadt).

Solvent systems. System G The lower phase of $CH_2Cl_2/CH_3OH/15\%$ strength ammonium hydroxide in the ratio 1/1/1, system E $CH_2Cl_2/CH_3OH$ 20% strength ammonium hydroxide in the ratio 8/4/1; parts by volume in each case.

EXAMPLE 1

N-D-Glucopyranosyl-oleamide 3 g of 2,3,4,6-tetra-O-acetyl-3,D-glucopyranosylamine were dissolved in 25 ml of tetrahydrofuran and, after addition of 3.45 g of sodium carbonate, 2.24 g of oleoyl chloride dissolved and in 5 ml of tetrahydrofuran (THF) were added dropwise, with vigorous stirring and cooling at 0° C. After completion of reaction (checked by thin-layer chromatography=TLC in the system toluene:acetone=4:1), the precipitate was filtered off, the filtrate was evaporated in vacuo and dried. For the O-deacetylation, the crude product thus obtained was dissolved in 200 ml of a solution of methanol/triethylamine/water=4:3:1 (parts by volume) and left at room temperature for 15 hours. The mixture was then evaporated in vacuo and the residue was chromatographed on silica gel. The title product obtained in this manner had an Rf value of 0.46.

EXAMPLE 2

N-Benzyl-$\beta$-D-glucopyranosylamine 50 g of D-glucose were dissolved in 1,000 ml of hot ethanol and, after addition of 89 g of benzylamine, were left at room temperature for 48 hours. The mixture was then cooled with ice and the product was precipitated with petroleum ether. It was filtered off with suction, washed with ether and dried in vacuo.

$^1H$ NMR in $CD_3OD: \delta = 7.33$ broad singlet phenyl-H.

EXAMPLE 3

N-Benzyl-N-glucopyranosyl-acetamide 1 g of the compound from Example 2 was acetylated in 10 ml of absolute pyridine at 0° C. with 6 ml of acetic anhydride at room temperature. The mixture was worked up as usual and 1 g of N-acetyl-tetra-O-acetyl derivative was obtained.

$^1$H NMR in CD Cl$_3$: δ=1.9–2.1 m 5×C$\underline{H}_3$—CO—.

For the O-deacetylation, 500 ml of the pentaacetate were deacetylated in absolute methanol with 10% sodium methylate and worked up as usual. The product was obtained as an amorphous solid.

$^1$H NMR in CD$_3$OD: δ=7.1–7.4 phenyl-H.

EXAMPLE 4

N-Dodecyl-β-D-glucopyranosylamine 18 g of glucose were stirredd in 50 ml of ethanol at 70° C., then 18.5 g of dodecylamine were added, the mixture was heated further until it was a clear solution, allowed to cool down to room temperature and, after 20 hours, the precipitated crystals were filtered off with suction. They were washed with ethanol and ether and dried in vacuo.

Yield=24 g.

Elementary Analysis (C$_{18}$H$_{37}$NO$_5$=347). Calculated: C=62.2%, H=10.6%, N=4.0%. Found: C=62.2%, H=10.6%, N=4.2%.

EXAMPLE 5

N-Dodecyl-N-β-D-glucopyranosyl-acetamide

The preparation was carried out in analogy to Examples 2 and 3 with an amount of N-dodecylamine used being equivalent to the amount of N-benzylamine used in Example 2.

Elementary Analysis. Calculated: C=61.7%, H=10.0%, N=3.6%. Found: C=60.8%, H=9.9%, N=3.8%.

EXAMPLE 6

N-Glucopyranosyl-N-propyl-oleamide 11 g of N-propyl-D-glucopyranosylamine were stirred in 90 ml of tetrahydrofuran (THF) with 21 g of sodium carbonate, then 1 equivalent of oleoyl chloride in 20 ml of THF was added dropwise slowly with cooling. After completion of N-acylation (checked by TLC in the solvent system CH$_2$Cl$_2$/CH$_3$OH=13:1), the precipitate was filtered off with suction, washed with THF and the filtrates were evaporated in vacuo and the syrup obtained was chromatographed on silica gel for final purification. Development of the column with CH$_2$Cl$_2$/CH$_3$OH was 15:1.

The fractions which contain the pure title compound were combined. The solvent was removed in vacuo.

Yield: 3.3 g.

Rf value: 0.34 in CH$_2$Cl$_2$/CH$_3$OH=15.1.

$[α]_D^{20}$=+7.5° (c=1.0 CH$_2$Cl$_2$).

EXAMPLE 7

N-Glucopyranosyl-N-hexyl-oleamide

The preparation was carried out as described in Example 6 starting from N-hexyl-D-glucopyranosylamine in an amount equivalent to the N-propyl-D-glucopyronosylamine used in the reference example.

Column chromatography with CH$_2$Cl$_2$/CH$_3$OH=13:1.

Yield: 9.2 g of pure product.

Rf value=0.38 in CH$_2$Cl$_2$/CH$_3$OH=13:1.

$[α]_D^{20}$=+5.8° C. (c=0.94 in CH$_2$Cl$_2$).

EXAMPLE 8

N-Glucopyranosyl-N-(n-3,3,3-trifluoropropyl)oleamide 3.6 g of glucose and 0.8 ml of 0.5N hydrochloric acid and 4.6 g of n-3,3,3-trifluoropropylamine were heated with stirring at 75° C. for 25 minutes. After cooling down, the N-glucoside crystallised out, was washed with ether and dried in vacuo.

Yield: 4.1 g.

The N-acylation with oleoyl chloride was carried out in analogy to Example 6. Column chromatography with CH$_2$Cl$_2$/CH$_3$OH=15.1.

Yield: 2.7 g.

$[α]_D^{20}$=7.6° (c=1.0 in CH$_2$Cl$_2$).

EXAMPLE 9

N-(2-Ethylhexyl)-N-glucopyranosyl-oleamide

The reaction of glucose with 2-ethylhexylamine was carried out in analogy to Example 8. The N-acylation with oleoyl chloride was carried out in analogy to Example 6.

Column chromatography with CH$_2$Cl$_2$/CH$_3$OH=15:1.

Rf value of the title compound: 0.44 in CH$_2$Cl$_2$/CH$_3$OH=15/1.

EXAMPLE 10

N-(3-Butoxypropyl)-N-glucopyranosyl-oleamide

Preparation of the N-glycoside and N-acylation as described for Example 8 or Example 6.

Rf value: 0.29 solvent system CH$_2$Cl$_2$/CH$_3$OH=10/1.

EXAMPLE 11

N-Dodecyl-N-glucopyranosyl-stearamide 100 g of N-dodecyl-β-D-glucopyranosylamine from Example 4 were dissolved in 765 ml of THF and, in the presence of 32 g of triethylamine, 80 g of stearoyl chloride were added dropwise with cooling.

For working up, the mixture was filtered and the solvent was removed in vacuo.

N-Dodecyl-N-glucopyranosyl-oleamide was repared likewise.

EXAMPLE 12

N-Decyl-N-glucopyranosyl-oleamide 18 g of D-glucose and 50 ml of ethanol were stirred with 15.7 g of decylamine at 70° C. until the solution was clear. It was then allowed to cool down to room temperature, and after 4 hours, the crystals were filtered off with suction and washed with ethanol and ether.

Yield: 20 g.

This was stirred in 166 ml of THF with 22.6 g of sodium carbonate. Then 19 g of oleoyl chloride in 20 ml of THF were slowly added dropwise at 25° C. After a further hour, the mixture was filtered off with suction, the filtrate was evaporated to a syrup in vacuo and the crude product was purified by column chromatography on silica gel with the eluting agent CH$_2$Cl$_2$/CH$_3$OH=13/1. Rf value of the title compound=0.53 in CH$_2$Cl$_2$/CH$_3$OH=13/2.

EXAMPLE 13

N-Glucopyranosyl-N-tetradecyl-oleamide

Preparation in analogy to Example 12.

Column chromatography with the eluting agent CH$_2$Cl$_2$CH$_3$OH=13/1.

$[α]_D^{20}$=+9.6 (c=1.0 DMF).

Elementary Analysis: Calculated: C=70.31 %, H=11.3%, N=2.16%. Found: C=69.4%, H=11.6%, N=2.1%.

EXAMPLE 14

N-Glucopyranosyl-N-hexadecyl-oleamide

Preparation and purification in analogy to Example 12.

Rf value: 0.25 mobilee phase CH$_2$Cl$_2$/CH$_3$OH=13/1.

EXAMPLE 15

N-Glucopyranosyl-N-octadecyl-oleamide 90 g of d-glucose and 135 g of octadecylamine in 1,000 ml of 2-propanol and 500 ml of water were heated to 50° C. with stirring until a clear solution had resulted. This was left overnight at room temperature. The product was now filtered off with suction, washed with alcohol and ether, dried and finally recrystallised from ethanol/THF. 10 g of this N-octadecyl-β-D-glucopyranosylamine were suspended in 80 ml of THF and, after the addition of 10 g of sodium carbonate 7 g of oleoyl chloride in 10 ml of THF were added dropwise. After quantitative reaction (TLC in CH$_2$Cl$_2$/CH$_3$OH=13/1), the mixture was worked up as described in Example 12. Column purification and eluting agent CH$_2$Cl$_2$/CH$_3$OH=13/1.

Rf value=0.35 solvent system CH$_2$Cl$_2$/CH$_3$OH=9/1.

EXAMPLE 16

N-Glucopyranosyl-N-octadecyl-stearamide

Preparation in analogy to Example 6 from N-octadecylglucopyranosylamine and stearoyl chloride.

Elementary Analysis: Calculated: C=72.5%, H=11.7%, N=2.0%. Found: C=71.7%, H=12.2%, N=2.0%.

EXAMPLE 17

N-glucosyl-N-octadecyl-dodecanamide

Preparation in analogy to Example 16 from N-octadecyl-β-D-glucopyranosylamine and dodecanoyl chloride.

$[\alpha]_D^{20} = +8°$ (C=1.0 dioxane).

EXAMPLE 18

N-Glucosyl-N-octadecyl-tetradecanamide

Preparation in analogy to Example 16 from N-octadecyl-β-D-glucopyranosylamine and tetradecanoyl chloride.

$[\alpha]_D^{20} = +9.5°$ (C=1.0 DMF).

Elementary Analysis: Calculated: C=71.8%, H=11.7%, N=2.1%. Found: C=71.3%, H=11.9%, N=1.9%.

EXAMPLE 19

N-(2-Acetamido-2-deoxy-D-glucopyranosyl)-N-octadecyl-oleamide 15 g of N-acetyl-D-glucosamine and 18.8 g of dodecylamine were heated in 50 ml of ethanol at 80° C. with stirring for 3 hours. The insolubles were filtered off hot, the filtrate was cooled down, the precipitated product was filtered off with suction and washed with ethanol and ether and 2.2 g of the 2-acetamido-2-deoxy-N-octadecylglucopyranosylamine thus obtained were stirred with 2 g of sodium carbonate in 17 ml of THF. Then 1.45 g of oleoyl chloride in 5 ml of THF were added dropwise.

Working up as described in Example 6.

Column chromatography with the eluting agent CH$_2$Cl$_2$/CH$_3$OH=20/1.

$[\alpha]^{20} = +9.2°$ (c=0.56 CH$_3$OH).

Elementary Analysis:

Calculated: C=72.8%, H=11.7%, N=3.8%. Found: C=72.9%, H=12.5%, N=3.3%.

EXAMPLE 20

N-Octadecyl-L-rhamnopyranosylamine 9 g of L-rhamnose and 13.5 g of stearylamine in 100 ml of 2-propanol and 50 ml of water were stirred at 50° C. until a clear solution had resulted. After 50 hours at room temperature, the crystals were filtered off with suction, washed with ethanol and ether and dried in vacuo. Yield: 17.4 g.

EXAMPLE 21

N-Octadecyl-N-rhamnopyranosyl-oleamide 7 g of the compound from Example 21 were acylated with oleoyl chloride as described in Example 6. Column separation in CH$_2$Cl/CH$_3$OH=13/1.

Elementary Analysis: Calculated: C=74.4%, H=11.9%, N=2.04%. Found: C=74.3%, H=12.0%, N=2.1%.

EXAMPLE 22

N-Octadecyl-L-fucopyranosylamine 3.26 g of L-fucose and 5.38 g of stearylamine in 20 ml of ethanol were heated to 70° C. with stirring until a clear solution had resulted. It was allowed to cool down and, after completion of crystallisation, the solid material was filtered off with suction and washed with ethanol and ether.

Yield after drying in vacuo: 4.4 g.

EXAMPLE 23

N-Fucopyranosyl-N-octadecyl-oleamide 2.9 g of the compound from Example 23 were acylated with oleoyl chloride as described in Example 6.

Column chromatography with the eluting agent CH$_2$Cl$_2$/CH$_3$OH=15/1.

Yield of pure product: 1.9 g.

RF value=0.44, solvent system as for column chromatography.

EXAMPLE 24

N-β,D-Arabinopyranosyl-N-octadecyl-oleamide 7 g of N-octadecyl-β,D-arabinopyranosylamine were acylated with oleoyl chloride as described in Example 6.

Column chromatography with eluting agent CH$_2$Cl$_2$/CH$_3$OH=20/1.

Yield of pure product: 2.3 g.

RF value=0.57, mobile phase CH$_2$Cl$_2$/CH$_3$OH=15/1.

$[\alpha]_D^{20} = +20°$ (c=1.03 CH$_2$CC$_2$).

EXAMPLE 25

N-β,D-Maltosyl-N-octadecyl-oleamide 3.04 g of N-octadecyl-β-D-maltosylamine were acylated with oleoyl chloride as described in Example 6.

Column chromatography in CH$_2$Cl$_2$/CH$_3$OH=10/1.

RF value: 0.24 mobile phase CH$_2$Cl$_2$/CH$_3$OH=8.1.

$[\alpha]_D^{20} = +22°$ C. (c=0.5 CH$_3$OH).

EXAMPLE 26

N-(4-Azido-4-deoxy-D-glucopyranosyl)-N-octadecyl-dodecanamide 3.09 g of 4-azido-4-deoxy-D-glucose were dissolved in 30 ml of isopropanol and 15 ml of water and, after addition of 4.05 g of octadecylamine, heated to 50° C.

The resulting solution was allowed to stand at room temperature overnight. The resulting solid material was filtered off, washed with a little ethanol and ether and dried.

2.3 g of this product were dissolved in 10 ml of THF, and 3 g of sodium carbonate and 1.2 g of dodecanoyl chloride, dissolved in 15 ml of THF, were added. After quantitative reaction, working up was carried out as described for Example 12.

Rf value: 0.27 in $CH_2Cl_2/CH_3OH=4:1$ (v/v).

EXAMPLE 27

N-(4-Acetamido-4-deoxy)-D-glucopyranosyl-N-octadecyl-oleamide 3 g of the compound from Example 26 in 30 ml of dioxane/methanol=2/1 and 3 ml of acetic anhydride were hydrogenated in the presence of 1.4 g of palladium-charcoal (5%) at normal pressure. After completion of the reaction (solvent system $CH_2Cl_2/CH_3OH=3/1$, the catalyst was filtered off and the filtrate was evaporated in vacuo.

Rf value: 0.18 ($CH_2Cl_2$/MeOH, 10:1 v/v).

EXAMPLE 28

N-(6-Deoxy-6-fluoro-D-glucopyranosyl)-N-octadecyl-oleamide 18.2 g of 6-deoxy-6-fluoro-D-glucose and 13.5 g of octadecylamine and 7 g of oleoyl chhloride were reacted and worked up as described in Example 15.

Rf value: 0.30 in $CH_2Cl_2/CH_3OH=9/1$.

EXAMPLE 29

N-(Methyl-D-glucopyranosyl)uronato-N-octadecyl-oleamide 15 g of D-glucuronolactone were dissolved in 150 ml of absolute methanol and allowed to stand with 3 ml of 1N sodium methanolate solution at room temperature for half an hour. The solution was then neutralized with an acid ion exchanger and evaporated. The resulting methyl glucuronate was reacted and worked up to give the title compound as described for Example 15.

Rf value: 0.32 ($CH_2Cl_2/CH_3OH=9.1$ v/v).

EXAMPLE 30

N-(Glucuronopyranosyl)-N-octadecyl-oleamide 2 g of the compound described in Example 30 were dissolved in 10 ml of dioxane and, after addition of 5 ml of 1N sodium hydroxide solution, were heated to reflux for 2 hours. After cooling down, the mixture was neutralised with dilute hydrochloric acid, evaporated in vacuo and the residue was stirred with 20 ml of methanol/dioxane=1/1. The mixture was then filtered and the filtrate was evaporated to a syrup.

Rf value 0.13 ($CH_2Cl_2/CH_3OH=7.1$, v/v).

EXAMPLE 31

N-(4-Amino-4-deoxy-D-glucopyranosyl)-N-octadecyl-lauramide 3 g of the compound from Example 26 in 30 ml of dioxane/methanol 2/1 were hydrogenated in the presence of 1.0 g of palladium-charcoal (5%). After completion of the reaction, the catalyst was filtered off and the solution was evaporated in vacuo.

Rf value: 0.39 $CH_2Cl_2$/MeOH 5:1.

EXAMPLE 32

N-(4-Lauramido-4-deoxy-D-glucopyranosyl)N-octadecy-lauramide 4.00 g of the compound described in Example 31 were dissolved in 30 ml of THF, 2.0 g of sodium carbonate were added and reacted with 1.42 g of dodecanoyl chloride in 10 ml of THF. After 30 min., the mixture was diluted with dichloromethane, filtered and the filtrate was evaporated in vacuo. The syrup was purified by column chromatography (mobile phase dichloromethane/methanol=15.1).

Rf value: 0.36 $CH_2Cl_2$/MeOH 10:1.

EXAMPLE 33

N-Glucopyranosyl-N-octadecyl-palmitamide

Preparation in analogy to Example 16 from N-octadecyl-glucopyranosylamine and palmitoyl chloride.

Rf value: 0.36 $CH_2Cl_2$/MeOH 9:1.

EXAMPLE 34

N-Octadecyl-N-glucopyranosyl-lauramide

Preparation in analogy to Example 16 from N-octadecyl-glucopyranosylamine and lauroyl chloride.

Rf value: 0.35 $CH_2Cl_2/CH_3OH$ 9:1.

EXAMPLE 35

N-Octadecyl-N-rhammopyranosyl-stearamide

Preparation in analogy to Example 22 from N-octadecyl-rhammopyranosylamine and stearoyl chloride.

Rf value: 0.39 $CH_2Cl_2/CH_3OH$ 9:1.

EXAMPLE 36

N-Octadecyl-(2-amino-2-deoxy-D-glucopyranosyl)amine hydrochloride 6.45 g of D-glucosamine hydrochloride were dissolved in 30 ml of isopropanol and 10 ml of water at 60° C. and 12.1 g of stearylamine were added. The resulting clear solution was stirred for a further 10 minutes and then cooled down to room temperature. The product which had crystallised out was filtered off with suction and initially washed with ethanol/water (5:2, v/v), then with ethanol and finally with ether. The residue was dried under high vacuum.

EXAMPLE 37

N-Octadecyl-N-(2-dodecoylamino-2-deoxy-D-glucopyranosyl)-dodecanamide 4.6 g of the compound described in Example 37 were suspended in 120 ml of tetrahydrofuran, and 22.6 g of sodium carbonate were added. 4.2 g of dodecanoyl chloride in 20 ml of tetrahydrofuran were added dropwise to the stirred suspension. The batch was evaporated in vacuo, acetylated with 50 ml of pyridine and 25 ml of acetic anhydride, poured onto ice-water, taken up in dichloromethane and the orgaic phase is washed consecutively with dilute hydrochloric acid, saturated sodium bicarbonate solution and then with water, dried over sodium sulphate and evaporated in vacuo to a syrup. The syrup obtained was purified by column chromatography. (Mobile phase toluene/ethyl acetate=10:1, v/v). The solid material obtained (melting point 86°) was dissolved in absolute methanol, 20 mg of sodium methoxide were added and heated under reflux for 20 min. After completion of the reaction, the mixture was neutralized with acid ion exchanger and evaporated in vacuo.

Melting point: 78° C., Rf value. 0.64 in $CH_2Cl_2/MeOH=10/1$ (v/v).

EXAMPLE 38

N-Propyl-(2-amino-2-deoxy-D-glucopyranosyl)amine hydrochloride 21.5 g of glucosamine hydrochloride were suspended in 17.7 g of n-propylamine and heated at 70° until a clear solution resulted. The product precipitated on cooling down to room temperature.

EXAMPLE 39

N-Propyl-N-(2-oleoylamido-2-deoxy-D-glucopyranosyl)-oleoylamide 5.1 g of the compound descrived in Example 39 were suspended in 100 ml of tetrahydrofuran, and 12.7 g of sodium carbonate were added. Then 12 g of oleoyl chloride in 20 ml of tetrahydrofuran were added dropwise. After completion of the reaction, the batch was diluted with 50 ml of dichloromethane, filtered off from the sodium salt, washed with water, dried over sodium sulphate and evaporated in vacuo. The syrup obtained was purified by column chromatography (mobile phase dichloromethane/methanol 15/1, v/v).

Rf value: 0.37 in $CH_2Cl_2/MeOH$ 10:1.
$\alpha_D=17.9°$ (c=1.02 in dichloromethane).

EXAMPLE 40

N-Glucopyranosyl-N-tetradecyl-stearamide

Preparation in analogy to Example 12 from N-tetradecyl-glucopyranosylamine staroyl chloride. Rf value: 0.25 in toluene/acetone 1:1.

EXAMPLE 41

N-Dodecyl-N-(2-amino-2-deoxyglucopyranosyl)amine hydrochloride 46 g of dodecylamine were melted at 60° and 31 g of glucosamine hydrochloride were added with stirring. After cooling down to room temperature, the product precipitated out. The solid material was stirred thoroughly three times with ether and filtered off with suction and subsequently dried under high vacuum.

EXAMPLE 42

N-Dodecyl-N-(2-stearoylamido-2-deoxy-D-glucopyranosyl)-stearamide 5 g of the compound described in Example 41 were suspended in 100 ml of tetrahydrofuran, and 8.5 g of sodium carbonate and 8 g of stearoyl chloride in 20 ml of tetrahydrofuran were added. After completion of reaction, the mixture was worked up as described in Example 40. The crude syrup obtained was crystallised from ethyl acetate.

Melting point 67°; Rf value 0.42 in $CH_2Cl_2/MeOH$ 10/1.

EXAMPLE 43

N-Dodecyl-N-(2-lauroylamido-2-deoxy-D-glucopyranosyl)-lauramide 5 g of the compound described in Example were reacted with lauroyl chloride as described in Example 43.

Melting point 67°; Rf value 0.42 in $CH_2Cl_2/MeOH$ 10/1.

EXAMPLE 44

N-Octadecyl-N-(galactopyranosyl)amine 60 g of D-galactose were suspended in 330 ml of isopropanol and 170 ml of water and heated to 50°. After addition of 90 g of stearylamine, the mixture was stirred until all the amine had gone into solution. On cooling, the glycosylamine crystallised out. The solid material was filtered off with suction, washed consecutively with ethanol and with ether and dried in vacuo.

EXAMPLE 45

N-Octadecyl-N-(d-galactopyranosyl)-lauramide

Preparation from 8.4 g of the compound described in Example 44 and 4.4 g of dodecanoyl chloride in analogy to Example 11.

Rf value: 0.22 in toluene/n-propanol 4/1 (v/v).
$\alpha_d=11.4$ (c=0.93 in dichloromethane).

EXAMPLE 46

N-Tetradecyl-N-(D-galactopyranosyl)-oleamide

N-Tetradecyl-N-(D-galactopyranosyl)amine was prepared from 30 g of D-galactose and 53 g of tetradecylamine as described in Example 44. The galactosylamine was reacted with oleoyl chloride according to the compound described in Example 11.

Rf value: 0.26 in toluene/N-propanol 4/1 (v/v).
$\alpha_D=11°$ (c=1.0 in dichloromethane).

EXAMPLE 47

N-Octadecyl-N-mannopyranosylamine 20 g of D-mannose and 45 g of stearylamine were reacted as described in Example 44 to give the glycosylamine.

EXAMPLE 48

N-Octadecyl-N-(D-mannopyranosyl)-lauramide 8.6 g of the compound described in Example 47 were reacted with 4.4 g of dodecanoyl chloride as described in Example 11.

Rf value: 0.25 in toluene/n-propanol 4/1 (v/v).
$\alpha_D$ 11.3° (c=1.13 in dichloromethane).

EXAMPLE 49

N-Octadecyl-N-(D-mannopyranosyl)-tetradecanamide

Preparation from the compound described in Example 48 and tetradecanoyl chloride in analogy to Example 11.

Rf value: 0.26 in toluene/n-propanol 4/1 (v/v).
$\alpha=9.9°$ (c=1.0 in dichloromethane).

EXAMPLE 50

N-Tetradecyl-N-(D-mannopyranosyl)-oleamide 20 g of D-mannose and 35 g of tetradecylamine were reacted as described in Example 44 to give N-tetradecylmannopyranosylamine. In a second reaction step, the glycosylamine (7.5 g) was reacted with 6.0 g of oleoyl chloride as described in Example 11 to give the glycosylamide.

Rf value: 0.29 in toluene/n-propanol 4/1 (v/v)
$\alpha_D = 10.8°$ (c=1 in tetrahydrofuran)

EXAMPLE 51

2-Dodecoylamino-2-deoxy-D-glucopyranose 55 g of dodecanoyl chloride were dissolved in 170 ml of tetrahydrofuran and added dropwise, with vigorous stirring, to a solution of 54 g of D-glucosamine hydrochloride in 330 ml of aqueous sodium carbonate solution (20%). After completion of the addition of the acid chloride, the mixture was stirred for a further hour, then 500 ml of water were added to the batch and the solid material was filtered off with suction and washed with water. The residue was recrystallised from isopropanol/water 10/1 (v/v) and dried under high vacuum.

EXAMPLE 52

N-Dodecyl-N-(2-dodecoylamido-2-deoxy-D-glucopyranosyl)amine 45 g of dodecylamine and 75 ml of ethanol were added to 15 g of the compound described in Example 51 and heated to 70° with stirring. After a clear solution had formed, it was cooled down to room temperature and crystallised overnight. The precipitated solid material was filtered off with suction, washed once with ethanol and three times with ether and dried in vacuo.

EXAMPLE 53

N-Dodecyl-N-(2-dodecoylamido-2-decoxy-D-glucopyranosyl)-stearoylamide 4 g of the compound described in Example 53 are dissolved in 100 ml of tetrahydrofuran, and 4.8 g of sodium carbonate are added. 3.45 g of stearoyl chloride dissolved in 20 ml of tetrahydrofuran were added dropwise to this suspension with stirring. The mixture was stirred for a further 30 minutes then diluted with 50 ml of dichloromethane and the solid material was filtered off with suction. The residue was washed with dichloromethane. The organic solvent phases were combined and evaporated in vacuo. The syrup obtained was purified by chromatography. (Mobile phase: dichloromethane/methanol 20/1 (v/v).

Rf value: 0.55 in dichloromethane/methanol 10/1 (v/v).
$\alpha = 15.8°$ (c=1.05 in dichloromethane).

EXAMPLE 54

N-Dodecyl-N-(2-acetamido-2-deoxy-D-glucopyranosyl)-tetradecanamide 26 g of N-acetylglucosamine were dissolved in 100 ml of ethanol and 60 ml of water and heated to 60°. 37 g of dodecylamine were added and stirred until a clear solution was achieved. The glycosylamine crystallised out after cooling down to room temperature. The mass of crystals was filtered off with suction, washed with ethanol and then with ether and dried in vacuo. 3 g of the solid material were suspended in 50 ml of tetrahydrofuran, 3.3 g of sodium carbonate were added and 1.9 g of tetradecanoyl chloride in 10 ml of tetrahydrofuran were added. After completion of reaction, the mixture was diluted with 30 ml of dichloromethane, filtered and the filtrate was evaporated in vacuo. The syrup obtained was purified by chromatography (mobile phase dichloromethane/methanol 20/1, (v/v)).

Rf value: 0.21 in dichloromethane/methanol 10/1 (v/v).

EXAMPLE 55

N-Dodecyl-N-(2-acetamido-2-deoxy-D-glucopyranosyl)-stearamide 3 g of N-(2-acetamido-2-deoxy)dodecylamine, the preparation of which is described in Example 54, were reacted with stearoyl chloride as described in Example 55.

Rf value: 0.23 in dichloromethane/methanol 10/1 (v/v).

EXAMPLE 56

N-Octadecyl-N-(2-acetamido-2-deoxy-D-glucopyranosyl)-tetradecanamide

Preparation in analogy to Example 19 from N-acetylglucosamine, stearlyamine and tetradecanoyl chloride.

Rf value: 0.25 in toluene/isopropanol 4/1 (v/v).
$\alpha = 16.9°$ (c=1 in tetrahydrofuran).

EXAMPLE 57

N-Dodecyl-N-(D-mannopyranosyl)-stearamide

Preparation from D-mannose, dodecylamine and stearoyl chloride in analogy to Example 11.

Rf value: 0.28 in toluene/n-propanol 4/1 (v/v).
$\alpha = 11.4°$ (c=1 in tetrahydrofuran).

EXAMPLE 58

N-Dodecyl-N-(D-galactopyranosyl)-stearamide

Preparation from D-galactose, dodecylamine and stearoyl chloride in analogy to Example 11.

Rf value: 0.28 in toluene/n-propanol 4/1 (v/v).
$\alpha = 4.4°$ (c=1 in dichloromethane).

What is claimed is:

1. A compound of the formula I

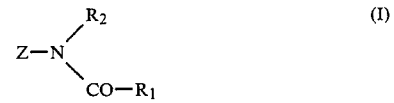

wherein Z denotes a glycosyl radical selected from the group consisting of rhamnopyranosyl, 6-deoxy-6-fluoro-D-glucopyranosyl, glucuronopyranosyl, 4-amino-4-deoxy-D-glucopyranosyl, 4-lauroylamido-4-deoxy-D-glucopyranosyl, 2-olanylamido-2-deoxy-D-glucopyranosyl, 2-stearoylamido-2-deoxy-D-glucopyranosyl glucopyranosyl, galactopyranosyl, mannopyranosyl, glucofuranosyl, ribofuranosyl, arabinopyranosyl or lyxopyranosyl, D-glycero-D-glucoheptopyranosyl, maltosyl, maltrotriosyl, maltotetraosyl, lactosyl, cellobiosyl, melibiosyl, 6-O-(α- or β-ribofuranosyl)-glucopyranosyl, 2-amino-2-deoxy-glucopyranosyl, 4-azido-4-deoxyglucopyranosyl, 4-stearoylamido-4-deoxy-D-glucopyranosyl, 4-dodecoylamido-4-deoxy-D-glucopyranosyl, 6-hexadecanoylamido-6-deoxy-D-galactopyranosyl, 2,6- diamino-2,6-dideoxyglucopyranosyl, 6,6'-diamino-6,6'-dideoxymaltosyl, 6-amino-6,6'dideoxylactosyl, 6-deoxymannopyranosyl, 2-deoxyribofuranosyl, fucosyl, 5-fluoro-5-deoxyribofuranosyl, 6-O-methylglucopyranosyl, 6-deoxy-6-thioglucopyranosyl, 3-deoxy-3-nitrogalactopyranosyl, galacturonic acid, methyl glucuronate, glucuronamide and N-dodecylglucuronamide bonded via the anomeric carbon atom, $R_1$ denotes an optionally substituted straight or branched $C_9$–$C_{21}$-alkyl or $C_7$–$C_{21}$-alkenyl radical, and $R_2$ denotes a straight-chain or branched or $C_9$–$C_{21}$-alkyl or $C_7$–$C_{21}$-alkenyl radical, or an aralkyl radical having up to 30 C atoms in which the aryl portion is mono- or bi-cyclic carbocyclic aryl and the alkyl portion contains 1 to 4 carbon atoms, which can be substituted by halogen.

2. A compound according to claim 1 wherein $R_1$ represents a radical selected from the group consisting of n-nonyl, n-decyl, n-undecyl, n-dodecyl, n-tridecyl, n-tetradecyl, n-pentadecyl, n-hexadecyl, n-heptadecyl, n-octadecyl, n-nonadecyl, docosyl, methyldecyl, i-propyldecyl, methyltridecyl, 6-heptenyl, 1-octenyl, 2-octenyl, 3-octenyl, 5-octenyl, 7-octenyl, 1-nonenyl, 3-nonenyl, 5-nonenyl, 7-nonenyl, 1-decenyl, 5-decenyl, 9-decenyl, 8-heptadecenyl, 1,3-heptadienyl, 2-4-heptadienyl, 1,3-octadienyl, 1,3-noadienyl, 2,4-decadienyl, 8-11-heptadecanedienyl and 8,11,14-heptadecanetrienyl.

3. A compound according to claim 1 wherein $R_2$ represents a radical selected from the group consisting of n-nonyl, n-decyl, n-undecyl, n-dodecyl, n-tridecyl, n-tetradecyl, n-pentadecyl, n-hexadecyl, n-heptadecyl, n-octadecyl, n-nonadecyl, docosyl, methyldecyl, i-propyldecyl, methyltridecyl, 6-heptenyl, 1-octenyl, 2-octenyl, 3-octenyl, 5-octenyl, 7-octenyl, 1-nonenyl, 3-nonenyl, 5-nonenyl, 7-nonenyl, 1-decenyl, 5decenyl, 9-decenyl, 8-heptadecenyl, 1,3-heptadienyl, 2-4-heptadienyl, 1,3-octadienyl, 1,3-nonadienyl, 2,4-decadienyl, 8-11-heptadecanedienyl and 8,11,14-heptadecanetrienyl myricyl, docosenyl, phenethyl and benzyl.

4. A compound according to claim 1 wherein Z is a monosaccharide radical which is optionally substituted by an acylamide group.

5. A compound of claim 1 which is N-Octadecyl-N-D-glucopyranosyl-Lauramide.

6. A compound of claim 1 which is N-Octadecyl-N-D-glycopyranosyl-oleamide.

7. A compound of claim 1 which is N-glucosyl-N-octadecyl-dodecaneamide.

8. A compound of claim 1 which is N-glucosyl-N-octadecyl-tetradecaneamide.

9. A compound of claim 1 which is N-octadecyl-N-(D-mannopyranozyl)-laurylamide.

10. A compound of claim 1 which is N-tetradecyl-N-(D-mannopyranosyl)-oleamide.

11. A compound of claim 1 which is N-dodecyl-N-(D-galactopyranosyl)-stearamide.

12. A compound according to claim 4 wherein Z is 2-acetylamido-2-deoxyglucopyranosyl or 4-acetamido-4-deoxyglucopyranosyl.

13. Process for the preparation of a compound of claim 1, formula I which comprises reacting a glycoside with an amine of the formula $R_2$—$NH_2$ to give a compound $$Z-NH-R_2,$$

Z and $R_2$ having the meanings mentioned in claim 1, then acylated with an acylating agent of the formula $R_1'CO$—X in which $R_1$ has the meaning mentioned in claim 1 and X represents its Leaving group customary in acylation reactions.

14. A pharmaceutical composition comprising an immune system antibody increasing amount of a compound of claim 1 in admixture with an inert pharmaceutical carrier.

15. A pharmaceutical composition of claim 1 in the form of a sterile or physiologically isotonic aqueous solution.

16. A medicament in dosage unit form comprising an immune system antibody increasing amount of a compound of claim 1 either alone or in admixture with an inert pharmaceutical carrier.

17. A medicament of claim 16 in the form of tablets, pills, dragees, capsules, ampoules or suppositories.

18. A method for stimulating the body's immune system defenese in a warm-blooded animal which comprises administering to said warm-blooded animal an immune system antibody increasing amount of a compound of claim 1 either alone or in admixture with an inert carrier or in the form of a medicament.

* * * * *

UNITED STATES PATENT AND TRADEMARK OFFICE
CERTIFICATE OF CORRECTION

PATENT NO. : 4,683,222  
DATED : July 28, 1987  
INVENTOR(S) : Peter Stadler, et al.

Page 1 of 3

It is certified that error appears in the above-identified patent and that said Letters Patent is hereby corrected as shown below:

| | |
|---|---|
| Col. 1, line 32 | Delete "n-penyl" and substitute --n-pentyl-- |
| Col. 2, line 32 | Delete "aroms" and substitute --atoms-- |
| Col. 3, line 27 | Correct spelling of --dodecoylamido-- |
| Col. 5, line 2 | End of line delete "or" and substitute --to-- |
| Col. 5, line 5 | Correct spelling of --o-nitrophenylsulphenyl-- |
| Col. 5, line 68 | After "formula" insert --I-- |
| Col. 6, line 65 | Correct spelling of --dimethylformamide-- |
| Col. 6, line 66 | After "except" delete "that" |
| Col. 14, line 8 | Delete "by" and substitute --be-- |
| Col. 15, line 10 | Delete "stirredd" and substitute --stirred-- |
| Col. 16, line 38 | End of line delete "repared" and substitute --prepared-- |
| Col. 16, line 66 | Delete "70.31%" and substitute --70.3%-- |
| Col. 17, line 6 | Delete "mobilee" and substitute --mobile-- |
| Col. 17, line 12 | Delete "d-" and substitute --D- -- |
| Col. 17, line 20 | After "carbonate" insert --,-- |
| Col. 17, line 38 | Delete "glucosyl" and substitute --Glucosyl-- |
| Col. 18, line 21 | Delete "Example 21" and substitute --Example 20-- |

UNITED STATES PATENT AND TRADEMARK OFFICE
CERTIFICATE OF CORRECTION

PATENT NO. : 4,683,222

DATED : July 28, 1987

INVENTOR(S) : Peter Stadler, et al.

Page 2 of 3

It is certified that error appears in the above-identified patent and that said Letters Patent is hereby corrected as shown below:

| | |
|---|---|
| Col. 18, line 41 | Delete "Example 23" and substitute --Example 22-- |
| Col. 19, line 39 | Correct spelling of --chloride-- |
| Col. 19, line 55 | Delete "9.1" and substitute --9:1-- |
| Col. 20, line 42 | Delete "Example 22" and substitute --Example 21-- |
| Col. 20, line 64 | Delete "Example 37" and substitute --Example 36-- |
| Col. 21, line 3 | Correct spelling of --organic-- |
| Col. 21, line 30 | Delete "descrived" and substitute --described-- |
| Col. 22, line 1 | Delete "Example 40" and substitute --Example 39-- |
| Col. 22, line 13 | Delete "43" and substitute --42-- |
| Col. 22, line 33 | Delete "$\alpha_d$" and substitute --$\alpha_D$-- |
| Col. 22, line 65 | Delete "48" and substitute --47-- |
| Col. 23, line 43 | Delete "Example 53" and substitute --Example 52-- |
| Col. 24, lines 17-18 | Delete "Example 55" and substitute --Example 54-- |
| Col. 24, line 27 | Correct spelling of --stearylamine-- |
| Col. 24, line 57 | Delete "olanylamide" and substitute --oleoylamido-- |

UNITED STATES PATENT AND TRADEMARK OFFICE
CERTIFICATE OF CORRECTION

PATENT NO. : 4,683,222

DATED : July 28, 1987

INVENTOR(S) : Peter Stadler, et al.

Page 3 of 3

It is certified that error appears in the above-identified patent and that said Letters Patent is hereby corrected as shown below:

| | |
|---|---|
| Col. 25, line 26 | Delete "noadienyl" and substitute --nonadienyl-- |
| Col. 25, line 37 | End of line, after "5" insert -- - -- |
| Col. 26, line 42 | Delete "defenese" and substitute --defenses-- |

Signed and Sealed this

Nineteenth Day of April, 1988

Attest:

DONALD J. QUIGG

Attesting Officer

Commissioner of Patents and Trademarks